United States Patent [19]

Turnidge

[11] Patent Number: 4,995,398
[45] Date of Patent: Feb. 26, 1991

[54] CORONARY ANGIOGRAPHY IMAGING SYSTEM

[76] Inventor: Patrick A. Turnidge, 5334 Quail St. NE., Salem, Oreg. 97305

[21] Appl. No.: 516,763

[22] Filed: Apr. 30, 1990

[51] Int. Cl.$^5$ ................................................. A61B 5/02
[52] U.S. Cl. ..................................... 128/668; 128/736; 128/664; 128/633
[58] Field of Search ............... 128/668, 664, 736, 666, 128/691, 633

[56] References Cited

U.S. PATENT DOCUMENTS

| 3,995,621 | 12/1976 | Fletcher et al. | 128/664 |
| 4,494,550 | 1/1985 | Blazek et al. | 128/664 |
| 4,817,622 | 4/1989 | Pennypacker et al. | 128/664 |
| 4,852,025 | 7/1989 | Herpichböhm | 128/633 |
| 4,900,162 | 2/1990 | Bekman et al. | 128/664 |
| 4,932,789 | 6/1990 | Egawa et al. | 128/664 |

Primary Examiner—Francis Jaworski
Assistant Examiner—George Manuel
Attorney, Agent, or Firm—Charles N. Hilke

[57] ABSTRACT

Thermography visually shows small temperature differences in either color or black and white. In heart by-pass operations, thermography is used to determine whether each by-pass is successful (i.e. the patency of the by-pass) and resulting flow directions and profusion during the course of the operation. The methods used include the use of scanning thermal camera, image processing, temperature differentials, and displaying images in real time.

31 Claims, No Drawings

CORONARY ANGIOGRAPHY IMAGING SYSTEM

THE INVENTION

This invention relates to the use of thermography on the human body, and more specifically, to the use of thermography during the course of by-pass heart surgery for the purpose of checking the successfulness both qualitatively and quantitatively for each bypass graft before closing the chest cavity.

2. Prior Art

In U.S. Pat. No. 3,335,716 a diagnostic thermography method was disclosed which included the coating of the skin with phosphor. An infrared imaging system is disclosed in U.S. Pat. No. 3,798,366. Finally, in U.S. Pat. No. 4,494,550 an infrared device is used to measure blood flow non-invasively through the skin.

Most of the prior art has occurred in medical research papers. In *Surgery* 1978; 84:858–64, the use of thermography in determining the patency of by-pass grafts is discussed. In *Cardiovascular Research* 1982; 16(3):158–62, 32 patients were evaluated by thermography during by-pass surgery for saphenous graft patency and blood flow.

While thermography has been used to measure the cooling effects of cardioplegic solutions and to assess coronary perfusion, it has never been applied as a routine, clinical tool during cardiac surgery, because the images have not been sufficiently precise to be useful. Instead, assessment of intraoperative graft patency is either assumed, or is based on passage of coronary probes, electromagnetic flow measurements or, most recently, angioscopy. Each of these methods, however, has its specific limitations.

Coronary probes are invasive, may be inaccurate in the sense that a probe may pass through but blood flow may still be restructured, and don't indicate the profusion field. Electromagnetic flow measurements are difficult to use and are sometimes inaccurate. Angioscopy is invasive, the viewing area is limited and doesn't show the profusion field.

Cine-angiography is generally used before surgery for determining whether surgery is necessary. A radioactive dye is released by a tube in an artery for a real time study of blood flow. Use of cine-angiography during surgery does not occur because of cost, danger to the patient, and the invasive nature of the test.

Thus, thermography is potentially an effective, non-invasive technique, if accuracy can be assured.

SUMMARY OF THE INVENTION

Thermal Coronary Angiography (TCA) is a technique that is capable of providing unique, clinically relevant information about epicardial coronary arteries and by-pass grafts during revascularization surgery. A thermal camera, focused on the exposed heart, and a digital image processor provides coronary images with high spatial (0.1 mm) and thermal resolution (0.1° C.), which can be displayed on a high resolution monitor in real time.

In patients undergoing saphenous vein (SV) and internal mammary artery (IMA) by-pass grafts, thermal angiograms are studied following the completion of the distal anastomoses, by injection of 20–30 ml of cold crystalloid cardioplegia into the proximal vein graft or by reperfusion with warmer blood after bulldog clamp release on the IMA graft. All data is recorded on videotape and digital image processing is performed immediately. TCA's provide details of graft and anastomotic patency, the direction of native coronary proximal (retrograde) and distal (antegrade) flow, and the presence of stenoses in the native coronary arteries. The area of regional epicardial perfusion for each graft is quantified by the image processor on the basis of distribution of the injectate through the epicardium.

Temperature differences between injectate and epimyocardium of greater than 4° C. results in high contrast images; in cases of low contrast images, processing provides enhanced image quality. Unsuspected stenoses can be detected at the site of distal anastomoses. Native coronarY stenoses are preciselY located in the recipient coronary arteries. Both the location and magnitude of the stenoses are confirmed by intraoperative calibration with coronary probes. These intraoperative assessments correlated directly with the preoperative cine-angiograms. In addition, delineation of graft perfusion beds correlated with the thermal angiographic findings of graft patency, and were of specific value in cases with excess epicardial fat around the coronary artery or when there were intramycardial coronary arteries; in these instances the angiographic images of coronary anatomy were obscured.

DETAILED DESCRIPTION OF THE PREFERRED EMBODIMENT

Thermography is a technique for recording pictorial format, with different color coded images small temperature differences between adjacent structures. Modern infrared imaging systems consist of a scanning thermal cameral, a video monitor, and a videotape recorder. Infrared radiation is detected and quantitated by special heat detectors in the scanner; it is then transformed to electric current and displayed as a thermal image on a monitor.

Although thermography has been used to measure the cooling effects of cardioplegic solutions and to assess coronary perfusion, it has never been applied as a routine, clinical tool during cardiac surgery, because the images have not been sufficiently precise to be useful. Instead, assessment of intraoperative graft patency is either assumed, or is based on passage of coronary probes, electromagnetic flow measurements or, most recently, angioscopy. Each of these methods, however, has its specific limitations.

Recent technical advances have led to the development of thermovision systems that are more accurate and easy to handle. These modern infrared thermography systems can be combined with digital image processors allowing image enhancement and quantitative measurements.

A liquid nitrogen cooled thermal camera with a 7° lens is used and an advanced version, electronically cooled camera with a 12° lens is also used. Aside from improved image quality, there is no apparent differences in the nature of the data obtained with one or the other camera. Both cameras are mounted on a tripod and focus directly on the exposed surface of the heart at a distance between 0.8 to 12 meters. The optimal angle for the camera was perpendicular (90°) to the heart surface. In practice, however, tilting of the electronically cooled camera was limited to a 70°–80° camera angulation. The camera settings are adjusted by the operator to the expected temperatures; the settings preferred are 20° C. for the vein and 30° C. for the IMA grafts with a range of ±10° C. Both camera systems provide a maximal spatial resolution of 9.1–0.22 mm and a thermal resolution of 9.6°–0.8° C. under these conditions. Images can be developed from the exposed surface to a depth of 4 mm.

The images are displayed either in black and white (B/W) or in color on a high resolution monitor in real time. Each color or gray scale level represents an isotherm. Selected images are enhanced and analyzed in real time using the attached image processor; the final images from each patient study are stored on floppy diskettes. Image enhancement is accomplished by image scaling, inventing, magnifying, low pass filtering, high pass filtering, or image subtraction. TCA's are obtained following completion of the distal anastomoses by injection of 30 ml of cold (8°–4° C.) crystalloid cardioplegia into the proximal vein grafts or by perfusion with warmer (25°–30° C.) blood after removing the bulldog clamp from the IMA grafts. Since these are the routine methods for infusing supplemental cardioplegia and for checking anastomoses for patency or leaks, TCA only required optimal exposure of the heart and focusing of the camera on the area of interest. The difference between the injectate and the epicardial temperature then allows delineation of the graft and native coronary anatomy. TCA's are used to evaluate graft patency, the character of anastomotic sites, native coronary anatomy including stenoses, flow directions, and regions of distal epimyocardial perfusion. Direction of flow is classified as antegrade and/or retrograde; and perfusion of branches and collaterals are established. Each of these observations are graded subjectively from 0–3, representing no flow to optimal flow. Regional perfusion distal to each graft is assessed, using the image processor; this is quantified by calculating the area of induced epimyocardial temperature change. TCA results are compared to intraoperative coronary probe calibrations and to the preoperative cine coronary angiogram. Cineangiograms and the catheterization reports are not reviewed until after the TCA is analyzed. Each real time TCA was graded 1–3 for image quality before image enhancement. These results are later correlated to camera angle, injectate-epicardial temperature difference, and the presence of fat or muscle covering the coronary arteries.

Data was entered in a specifically designed spreadsheet which allows complete intraoperative data storage and provided continuous updating, evaluation and statistical analysis of the data. This program is additionally installed on the same computer which was used to process images.

What is claimed is:

1. A method of thermal coronary angiography for assessing graft patency, coronary anatomy and perfusion fields in coronary by-pass surgery, which comprises:
   (a) positioning a thermal camera between 70° to 90° perpendicular to the exposed surface of the heart;
   (b) positioning the thermal camera a distance between 0.8 meters to 1.2 meters from the exposed surface of the heart;
   (c) setting the thermal camera to the expected temperatures such that expected temperatures are near one of the two ends of the scale;
   (d) injecting cold crystalloid cardioplegia into a proximal vein graft; and
   (e) recording and displaying images on a monitor in real time.

2. The method of claim 1 wherein the expected temperature is 20° C.

3. The method of claim wherein the temperature of cold crystalloid cardioplegia is 8° C. to 14° C.

4. The method of claim 1 wherein the amount of cold crystalloid cardioplegia is 20–30 ml.

5. The method of claim 1 wherein the temperature difference between the exposed surface of the heart and the cold crystalloid cardioplegia is greater than 4° C.

6. The method of claim 1 where temperature differences can be displayed to a depth of 4 mm.

7. The method of claim 1 additionally comprising:
   (f) enhancing said image by a thermal image computer.

8. The method of claim 7 wherein said enhancement is accomplished by image scaling.

9. The method of claim 7 where said enhancement is accomplished by inventing.

10. The method of claim 7 where said enhancement is accomplished by magnifying.

11. The method of claim 7 where said enhancement is accomplished by low pass filtering.

12. The method of claim 7 where said enhancement is accomplished by high pass filtering.

13. The method of claim 7 where said enhancement is accomplished by image subtraction.

14. The method of claim 1 additionally comprising:
   (g) stopping an image on the monitor.

15. The method of claim 1 additionally comprising:
   (h) storing said images.

16. The method of claim 15 where storing said images was on floppy diskettes.

17. A method of thermal coronary angiography for assessing graft patency, coronary anatomy and perfusion fields in coronary by-pass surgery, which comprises:
   (a) positioning a thermal camera between 70° to 90° perpendicular to the exposed surface of the heart;
   (b) positioning the thermal camera a distance between 0.8 meters to 1.2 meters from the exposed surface of the heart;
   (c) setting the thermal camera to the expected temperatures such that said expected temperatures are near one of the two ends of the scale;
   (d) releasing a bulldog clamp on the internal mammary artery;
   (e) reperfusing with warmer blood into the internal mammary artery; and
   (f) recording and displaying images on a monitor in real time.

18. The method of claim 17 wherein the temperature difference between the exposed surface of the heart and the warmer blood is greater than 4° C.

19. The method of claim 17 wherein the temperature of warm blood is 25° C. to 30° C.

20. The method of claim 17 wherein the expected temperature is 20° C.

21. The method of claim 17 additionally comprising:
   (g) enhancing said image by a thermal image computer.

22. The method of claim 21 wherein said enhancement is accomplished by image scaling.

23. The method of claim 21 where said enhancement is accomplished by inverting.

24. The method of claim 21 where said enhancement is accomplished by magnifying.

25. The method of claim 21 where said enhancement is accomplished by low pass filtering.

26. The method of claim 21 where said enhancement is accomplished by high pass filtering.

27. The method of claim 21 where said enhancement is accomplished by image subtraction.

28. The method of claim 17 additionally comprising:
(h) stopping an image on the monitor.

29. The method of claim 17 additionally comprising:
(i) storing said images.

30. The method of claim 29 where said storing said images is on floppy diskettes.

31. The method of claim 17 where temperature differences can be displayed to a depth of 4 mm.

* * * * *